United States Patent
Schneider et al.

(10) Patent No.: US 9,295,477 B2
(45) Date of Patent: Mar. 29, 2016

(54) DRIVE CONTROL DEVICE AND DRIVE CONTROL METHOD FOR A SURGICAL MOTOR SYSTEM

(71) Applicant: Aesculap AG, Tuttlingen (DE)

(72) Inventors: Jürgen Schneider, Tuttlingen (DE); Harald Konrath, Rottenburg-Hailfingen (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 14/414,987

(22) PCT Filed: Jul. 10, 2013

(86) PCT No.: PCT/EP2013/064615
§ 371 (c)(1),
(2) Date: Jan. 15, 2015

(87) PCT Pub. No.: WO2014/012833
PCT Pub. Date: Jan. 23, 2014

(65) Prior Publication Data
US 2015/0164515 A1    Jun. 18, 2015

(30) Foreign Application Priority Data

Jul. 20, 2012   (DE) .......................... 10 2012 106 589

(51) Int. Cl.
*H02P 1/04*         (2006.01)
*A61B 17/16*        (2006.01)
(Continued)

(52) U.S. Cl.
CPC .............. *A61B 17/1626* (2013.01); *H02P 6/14* (2013.01); *A61B 2017/00398* (2013.01)

(58) Field of Classification Search
CPC .............. H02P 1/04; H02P 6/14; H02P 1/18; A61B 17/1626

USPC ................. 318/254, 400.01, 400.12, 400.14, 318/400.15, 432, 700, 727, 799, 568.11, 318/568.12, 568.21; 388/815, 928.1, 930, 388/800, 825, 842, 848; 606/169, 170, 176, 606/180, 311

See application file for complete search history.

(56) References Cited

U.S. PATENT DOCUMENTS 5,689,159 A * 11/1997 Culp ..................... A61C 1/0015
                                                      318/400.18
6,017,354 A *  1/2000 Culp ................. A61B 17/32002
                                                      604/22
(Continued)

FOREIGN PATENT DOCUMENTS

DE         102 25 857 A1     1/2004
DE     10 2009 018 143 A1    10/2010
(Continued)

OTHER PUBLICATIONS

International Search Report issued in related International Application No. PCT/EP/2013/064615, dated Oct. 4, 2013.
(Continued)

*Primary Examiner* — Antony M Paul
(74) *Attorney, Agent, or Firm* — RatnerPrestia

(57) ABSTRACT

A drive control device for a surgical motor system includes a motor control unit for controlling an electric motor in an open and/or closed loop, the electric motor driving a surgical tool. In order to use the drive control device for the most varied application cases, a parameter specification device is provided upstream of the motor control unit. The parameter specification device determines the current medical application on the basis of a detected state or state history of the surgical motor system, in particular of the electric motor, selects a control mode which is suitable for the medical application, and gives the motor control unit the open or closed loop parameters that the open or closed loop control profile of the electric motor corresponds to the selected control mode.

11 Claims, 3 Drawing Sheets

(51) Int. Cl.
*H02P 6/14* (2006.01)
*A61B 17/00* (2006.01)

(56) References Cited

U.S. PATENT DOCUMENTS

| | | |
|---|---|---|
| 6,025,683 A | 2/2000 | Philipp |
| 7,422,582 B2 * | 9/2008 | Malackowski ..... A61B 17/1613 606/1 |
| 2005/0116673 A1 | 6/2005 | Carl et al. |

FOREIGN PATENT DOCUMENTS

| | | |
|---|---|---|
| EP | 2 324 779 A1 | 5/2011 |
| WO | WO 2006/012991 A1 | 2/2006 |

OTHER PUBLICATIONS

German Search Report with partial translation issued in related German Application No. 10 2012 106 589.6, dated Apr. 26, 2013.
International Preliminary Report on Patentability with English translation issued in related International Application No. PCT/EP2013/064615, dated Jul. 11, 2014.

* cited by examiner

DRIVE CONTROL DEVICE AND DRIVE CONTROL METHOD FOR A SURGICAL MOTOR SYSTEM

RELATED APPLICATIONS

This application is filed under 35 U.S.C. §371 as the U.S. National Phase of International Application No. PCT/EP2013/064615, filed Jul. 10, 2013, which claims the benefit of priority of German Application DE 10 2012 106 589.6, filed Jul. 20, 2012, the contents of both applications being incorporated by reference herein in their entirety.

FIELD

The present invention relates to a drive control device for a surgical motor system comprising a motor control unit for controlling an electric motor in an open and/or closed loop, said electric motor driving a surgical tool. A further aspect of the invention relates to the motor system itself. Further, the present invention relates to a method of triggering a surgical motor system, in which the surgical tool is driven by an electric motor which is controlled by means of a motor control unit in an open and/or closed loop.

BACKGROUND

Surgical motor systems of the generic kind are known in numerous variants, in particular together with tools in the form of drilling and milling machines or saws. They are operated by the motor control unit generating control signals for the electric motor, to operate it with a specific rotational speed which can be set by the drive control device. Depending on the type of the electric motor, rotational speeds of up to 80000 revolutions per minute may be achieved. A motor system of this type is especially cost-effective and low-maintenance if the electric motor is a brushless DC motor which has at least two motor windings apart from the rotor.

Drive control devices for surgical motor systems of the generic kind are known, for example, from WO 2006/012991 A1 or DE 10 2009 018 143 A1. With these known drive control devices, the rotational speed of the surgical tool concerned is controlled in a closed loop, wherein e.g. a pulse width modulation (PWM) or a space vector pulse width modulation (SVPWM) is used. Compared to the conventional pulse width modulation, the SVPWM method has the advantage that all motor windings can be energized at the same time, so that a smooth and jerk-free operation of the electric motor is possible also with particularly low rotational speeds.

From EP 2 324 779 A1 a surgical motor system is known intended for various medical applications and comprising a drive control unit including an electronic circuit serving to control the rotational speed of the motor system in an open and/or closed loop. The way of controlling the rotational speed in an open and/or closed loop changes depending on the tool holder which is attached to the surgical motor system.

Apart from their smooth operation, these known closed-loop control methods are distinguished above all by the fact that the respective rotational speed can be readjusted very fast. However, it has turned out that e.g. in the event of extreme load changes a very quick readjustment of the rotational speed does not only bring advantages, as can be seen from the following comparison:

If e.g. an uncontrolled motor operated with compressed air experiences a short-term drop of the rotational speed during driving a milling cutter due to it being possibly caught, this will result in the motor speed rising again after the milling cutter has come loose. An additional temperature rise will not be produced here.

On the other hand, if such a milling cutter is driven by an electric motor controlled in a closed loop, the motor control unit performs the readjustment in such a situation within very short time to counteract the sharp drop of the rotational speed. This results in problems in particular if the tool gets caught several times in succession and the rotational speed has to be readjusted again and again. If the current profile is examined in more detail in such a situation, additional energization impulses will be measured ($I^2 \times R$). As a consequence, these very quick, dynamic closed-loop control processes are accompanied by additional losses. Due to the continuous readjusting and the associated current peaks, the electric motor produces a larger amount of heat and there is the risk that it will overheat.

There are many applications (e.g. in craniotomy) in which such a quick readjusting is desired or even required, where the depicted disadvantage of the additional losses may be simply accepted due to the comparably short activation times in craniotomy. However, there are applications such as the time-consuming process of milling off a bone segment in which the focus is not so much on the quick readjustment but rather on the lowest possible thermal losses.

If the above-mentioned drive control devices known e.g. from WO 2006/012991 A1 or DE 10 2009 018 143 A1 are used in a process of milling off a bone segment, there is the risk that the electric motor will be overheated or possibly even damaged. Accordingly, the field of use of the previously known drive control devices for surgical instruments or apparatus is limited to specific purposes for reasons of safety. This is why different surgical motor systems or those comprising respectively suitable drive motors are used hitherto depending on the field of application. This impedes the handling and increases costs as well. It would be desirable, however, to use one motor system for a wide variety of medical applications.

SUMMARY

The invention is based on the object to further develop a drive control device such that the field of use of the associated surgical motor system can be enlarged. Likewise, a corresponding control method as well as a surgical motor system are to be provided, too.

This object is achieved with regard to the drive control device, the surgical motor system, and the method in accordance with the invention.

The invention suggests to provide a parameter specification device which is arranged upstream of the motor control unit and allows to set the open or closed loop parameters of the motor control unit such that the open or closed loop control profile of the electric motor can be adapted to the respective state of the electric motor. Instead of using different motor systems for different applications, the invention is based on the idea to vary the control mode or the open or closed loop control profile of the electric motor in such a manner that it is optimally adapted to the respective application so as to allow a larger range of use of the employed motor system. The basis for the selection of the open or closed loop parameters is the detected state or state history of the electric motor, by means of which the parameter specification device is capable of determining the current medical application. With a suitable selection of parameters, it will be achieved that the resultant open or closed loop control profile safely prevents an overload such as an unallowable temperature rise of the electric motor. The triggering process according to the invention may therefore be used for the most varied surgical purposes without the need of having different motors available. The various control modes or triggering profiles may be realized by pure software engineering solutions, whereas the hardware, i.e. the control electronics and the motor, may remain unchanged. Thus, the manageability is clearly improved and the costs are reduced correspondingly.

By altering the open or closed loop parameters, the open or closed loop control profile of the electric motor can be changed such that the resultant torque/speed characteristic is optimally adapted to the respective load condition.

In the sense of the invention, a control mode has an influence on or alters the set points or pilot values and/or the open or closed loop control characteristic itself. In the event of an application case where a quick readjustment it is not required (as e.g. during milling off a bone segment), the P proportion can be reduced and the I proportion can be increased in the control process so as to avoid high current peaks. As an alternative or in addition, the level of the maximum current can be lowered as a whole. Further, the parameter specification device allows to accordingly lower the set point or the target rotational speed, in particular after having exceeded a critical current or if its overrun is to be expected.

It is preferred that the electric motor or the tool can be operated first according to a default control mode or a manually adjustable control mode and then can be changed or switched to a more suitable control mode depending on the detected state or the identified current medical application.

Depending on the application case, it is also possible to switch between an operation with rotational speed regulation and an operation without rotational speed regulation (pure open-loop control), to use different control parameters for the rotational speed regulation or to adapt the magnitude of the set point depending on the situation with unchanged control parameters. A further alternative is to alter the internal resistance of the motor, in which the output voltage for the motor is correspondingly lowered or increased in proportion to the measured current.

The different open or closed loop control profiles are deposited in the form of control modes from which a suitable one can be selected depending on the situation. According to the invention, selecting and switching are performed in an automated manner.

According to the invention, the respective state of the surgical motor system is dynamically detected in order to be able to change the open or closed loop control profile corresponding to the respective demands quasi in continuous fashion.

According to one embodiment, it is possible to deposit a plurality of different control modes, i.e. open and/or closed loop parameters or characteristic curves of the motor, which each are associated to corresponding medical applications. Depending on the detected state or the detected state history of the electric motor, the parameter specification device is then able to select the suitable control mode from these.

As an alternative or in addition, the selection of the control mode may be performed depending on the employed surgical tool or tool adapter. Due to the preferably automatic detection, one or more control modes suitable for the tool can be selected. To give an example, different tools are operated with different rotational speeds, e.g. with a maximum of 20000 rpm or a maximum of up to 80000 rpm. The identification of the tool makes sure that the maximum motor speed and/or the maximum torque are limited in corresponding fashion.

Each control mode may have a predetermined torque/speed characteristic of the electric motor associated to it.

Instead of or in addition to permanently deposited control modes, a suitable control mode can be generated on the basis of a training algorithm.

In one embodiment, the control mode may also be selected as a function of a detected control incidence per unit of time, being indicative of an application with many load fluctuations.

It may further be of advantage to determine the respective state of the surgical motor system by a preferably continuous detection of the respective instantaneous value of motor current and motor voltage of the electric motor. If a closed-loop controller is provided as a motor control unit anyway, this has the advantage that the sensors required for said control process are already available, so that no additional costs are produced.

Further or as an alternative, the respective state of the surgical motor system can be determined by a preferably continuous detection of a temperature of the electric motor (M), with the option that in the absence of a corresponding sensor the temperature can also be indirectly detected by integration of the respective instantaneous values of motor current and motor voltage.

It is also advantageous if at least one control mode provides for a rotational speed regulation of the electric motor and at least one other control mode does not provide for a rotational speed regulation of the electric motor. In this way, it is possible to simulate by software engineering a controlled as well as an uncontrolled operation, in particular the uncontrolled operation of a compressed air motor.

In the open and/or closed loop control method, the motor control unit may carry out either a pulse width modulation or a space vector pulse width modulation (SVPWM) in which all motor windings are energized simultaneously.

In order be able to identify the state of the electric motor, a rotor position determination means may be provided for determining a rotor position of the electric motor; for the purpose of determining the position of the rotor of the electric motor, at least one of the motor windings is cut off from a power supply for a predetermined time interval. With a rotational speed of 80000 rpm and three motor windings which are cut off one by one, the position of the rotor and the electromotive force can be measured 4000 times per second. This allows to detect the state of the electric motor in very short time and to select a corresponding control mode.

A surgical motor system according to the invention comprises an electric motor for driving a surgical tool which can be detachably connected to it directly or indirectly, in particular by interposing a tool adapter or handpiece, as well as a drive control device as described above.

The surgical motor system may also include a rotational speed detection means for detecting the actual speed of the electric motor, in particular Hall sensors, and/or a handpiece or tool identification means. This allows for an automatic identification of the state of the electric motor and the employed tool or tool system and the selection of a corresponding control mode.

The method, according to the invention, of an open and/or closed loop control of an electric motor (M) of a surgical motor system which drives a surgical tool, is characterized by the following steps: detecting a state and/or state history of the surgical motor system, in particular of the electric motor; selecting a control mode on the basis of the detected state or state history; and adjusting the open or closed loop parameters such that the open or closed loop control profile of the electric motor corresponds to the selected control mode.

BRIEF DESCRIPTION OF THE DRAWING FIGURES

The invention is explained below on the basis of the description of an embodiment with reference to the drawings in which.

DETAILED DESCRIPTION

Figure 1:
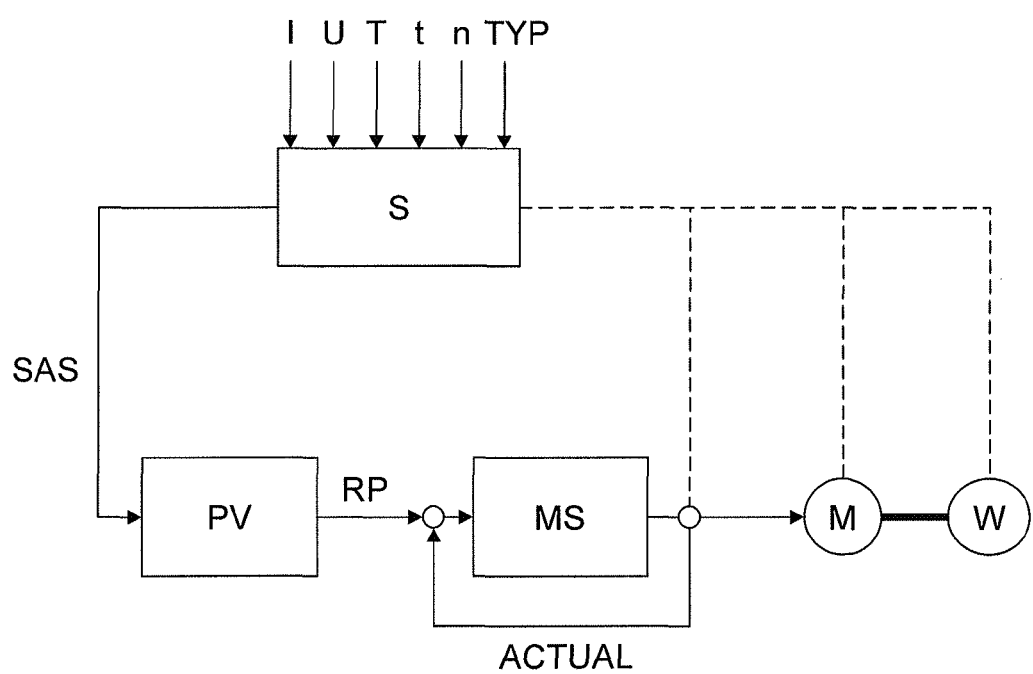
FIG. 1 shows a block diagram of a surgical motor system comprising a drive control device according to the invention.

According to FIG. 1, the surgical motor system according to the invention comprises an electric motor M which is mechanically coupled to a tool W via a tool clutch and drives it; the tool W may be a drill, a milling cutter, a saw, a craniotomy or trepanation tool, a shaver or another surgical tool. The basic triggering of the tool is performed via a (not shown) hand or foot-operated control unit. Here, the electric motor M is triggered by a motor control unit MS. For each phase or winding of the electric motor M, said motor control unit generates either a pulse width modulation signal (PWM) or a space vector pulse width modulation signal (SVPWM); in the latter case, all motor windings are energized simultaneously.

If the motor control unit MS is in the mode of controlling the rotational speed in closed-loop fashion, its input is supplied with a real value signal IST which indicates the instantaneous value required for controlling the rotational speed in closed-loop fashion. Sensors (not shown), in particular in the form of Hall sensors, are provided for the detection of the rotational speed. If the closed-loop control carried out by the motor control unit MS requires any other feedback values, such as in particular the supplied current or the applied voltage, the real value signal IST contains corresponding information.

According to FIG. 1, a parameter specification device PV is provided upstream the motor control unit MS and generates open or closed loop parameters RP which are applied as a pilot value at the input of the motor control unit MS in addition to the real value signal IST. Based on the type of the respectively applied open or closed loop parameters RP, the open or closed loop control profile provided by the motor control unit MS is adjusted or set. First, the open or closed loop control of the tool W is performed according to a default control mode or a control mode manually input by a user.

According to FIG. 1, a sensor system S is further provided whose inputs are fed with the signals of several sensors, namely a signal I representing the present motor current, a signal U representing the motor voltage as well as a rotational speed signal n. The latter represents the current rotational speed of the electric motor M and is produced for instance by a Hall sensor, as already mentioned. Further, there may be provided a signal T which is generated by a temperature probe and indicates the current temperature of the electric motor M. As the respective machines and tools are very small in the surgical field, placing such a temperature probe as well as transmitting its output signal T often entails large problems. Therefore, the temperature signal T is determined in one embodiment of the invention by integrating the detected instantaneous values of motor current and motor voltage of the electric motor M. Eventually, the duration of the current medical or surgical treatment, i.e. the current duration of the current tool insert may be measured and output as a time signal t.

Moreover, the motor system may additionally comprise a sensor system which automatically identifies the kind of the currently used tool and delivers a corresponding type signal TYP. According to FIG. 1, the sensor system produces a sensor output signal SAS which is supplied to the parameter specification device PV.

In the parameter specification device PV or another storing device, application-related state variables and histories of the input signals U, I, n, T; t, TYP are deposited. By means of various test series and measurement series in the forefront or with the aid of a training algorithm, it is possible to determine which ones of the state variables and histories are typical for the respective tool inserts. This allocation of state variables and medical application enables the parameter specification device PV to determine the current application on the basis of the present input variables or measured values.

As described at the outset, all applications and tool inserts require different drives. In case of milling applications, for instance, smaller motor currents in the range from at most 1 A and moments of at most 1.5 Ncm can be expected, whereas in craniotomy currents of up to approximately 3.5 A and moments of up to 3.5 Ncm are more likely to occur.

Apart from the automatic identification of the current application, the parameter specification device PV selects the appropriate control mode in a second step. This correlation between application and control mode is also deposited in the parameter specification device PV or another memory device.

Figure 2:
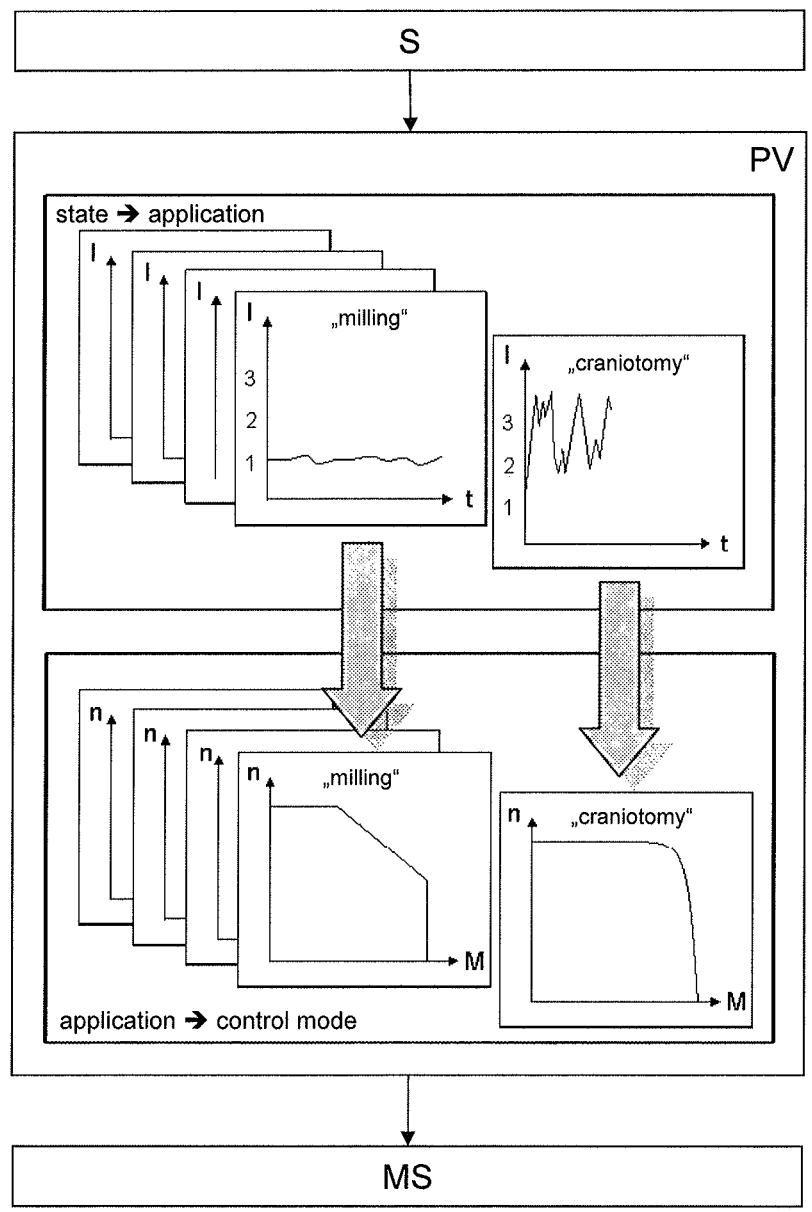
FIG. 2 shows a block diagram of a parameter specification device PV according to the invention.

Said two steps carried out by the parameter specification device PV are schematically shown in the FIG. 2 by taking the example of "milling" and "craniotomy" on the basis of a temporal progress of the current I. In order to enhance the allocation reliability, several or all of the measured or determined values may be compared with corresponding deposited profiles and evaluated.

Having selected an application-oriented control mode, the parameter specification device PV delivers corresponding open and/or closed loop control parameters to the motor control unit MS and in this way alters the open or closed loop control behavior of the motor control unit MS. Thus, the parameter specification device PV automatically switches from the control mode (which in the first instance has been set by default or manually) to a more suitable control mode. This means that the parameter specification device PV is able to provide the motor control unit MS with such an open or closed loop control profile which is best suited to the current load condition of the electric motor M represented by the signals U, I, n, T, t and/or TYP. If for instance, the measured values or their temporal progression indicate that the surgical tool W is about to carry out a craniotomy, the parameter specification device PV adjusts on the motor control unit MS a closed-loop control profile which results in the motor characteristic 1 in FIG. 3, for example, i.e. the rotational speed of the electric motor M is kept constant at full power or is readjusted as quickly as possible. On the other hand, if it is detected that the activity carried out with the tool W is more likely the time-consuming process of milling off a bone segment, it is preferred to set one of the characteristic curves 3 to 5 in FIG. 3 in which the temperature rise of the electric motor M is much smaller.

Figure 3:
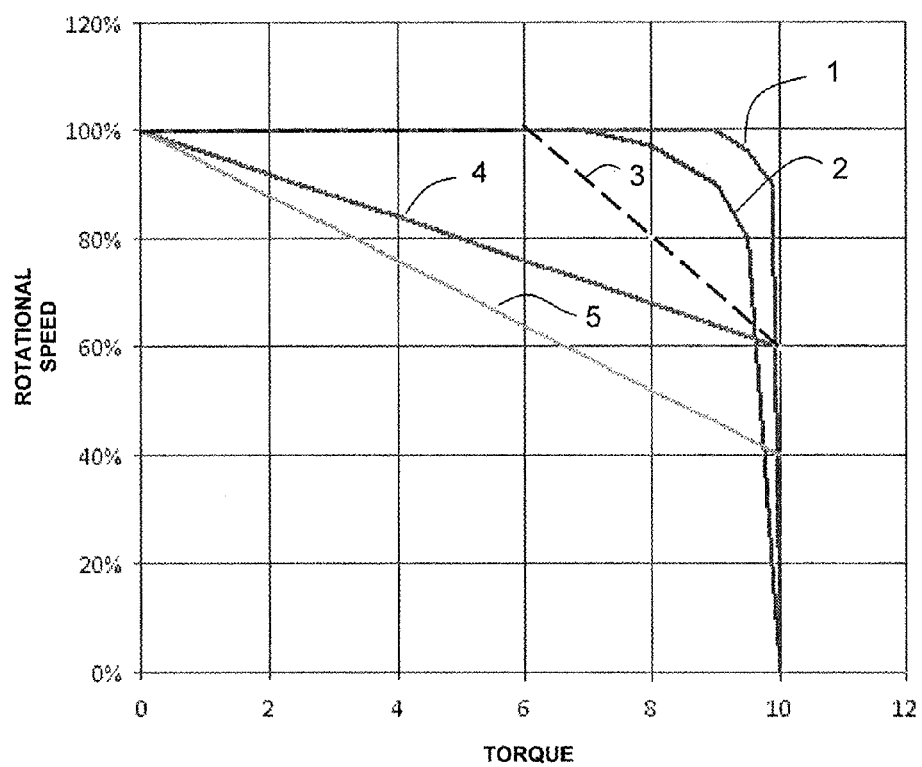
FIG. 3 shows several characteristic curves which are realized as an open or closed loop control profile of the surgical motor system.

FIG. 3 exemplarily shows some motor characteristics in the form of the torque/rotational speed curve of the electric motor M, imposed by the motor control unit MS on the electric motor M as a function of the respective open or closed loop parameter RP of the parameter specification device PV. The characteristic designated with 1 is a rotational speed regulation characteristic in which the rotational speed can be kept constant except for a very small range starting from 9.5 Ncm. The characteristic curves denoted with 2 and 3 are rotational speed regulation characteristic curves in which the rotational speed starts to drop at a somewhat already earlier point in time, as can be seen in the diagram. With the characteristic curves designated with 4 and 5, however, a rotational speed regulation is not performed, as can be directly seen.

Depending on the case of application or the identified load condition of the surgical tool W, it may be reasonable to set the open or closed loop control profile of the motor control unit MS in some other way than apparent from the diagram of FIG. 3. The following open or closed loop control profiles are cited as examples:

1.) No use of a rotational speed regulation;
2.) Use of a rotational speed regulation with modified control parameters;
3.) Rotational speed regulation with best coordinated parameters, but adjust the set point of the rotational speed regulation depending on the situation;
4.) Alteration of the internal resistance of the motor:

In proportion to the measured motor current, the motor control unit MS lowers the output voltage for the electric motor M as follows.

$$U_{corrected} = U_{normal} - \Delta U$$

$$\Delta U = R \times I_{motor}$$

For an electric motor M with a high internal resistance, the voltage $\Delta U$ drops across the internal resistance of the winding. This is why the motor control unit MS delivers a voltage reduced by $\Delta U$, in order to achieve the same effect in a motor whose internal resistance is not so high.

5.) Implemented in the parameter specification device PV is a suitable training algorithm which sets the control profile of the electric motor in accordance with training the load conditions of the electric motor. By way of example, the parameter specification device PV detects the temperature rise of the motor via a temperature model. Especially in the event of a prolonged operation of the motor as is the case during milling, a conclusion is made that the tool W is used for milling operations, whereupon the motor control unit MS is switched to the best suited open or closed loop control profile.

As the signals produced by the sensor system S are required as feedback values by the motor control unit MS depending on the type of the latter (as indicated in FIG. 1 by the broken line), a single sensor system is enough for the motor control unit MS and the parameter specification device PV according to the invention. As a motor control unit MS of the type required here usually includes a sensor system already, the parameter specification device PV according to the invention does not need additional sensors in most cases.

The invention claimed is:

1. A drive control device for a surgical motor system comprising a motor control unit for controlling an electric motor in an open and/or closed loop, said electric motor driving a surgical tool,
   wherein
   a parameter specification device which is provided upstream of the motor control unit and determines the current medical application on the basis of a detected state or state history of the electric motor of the surgical motor system, selects a control mode which is suitable for said medical application and gives the motor control unit such open or closed loop parameters that the open or closed loop control profile of the electric motor corresponds to the selected control mode.

2. The drive control device according to claim 1, wherein the parameter specification device selects the control mode from a plurality of control modes which are deposited and assigned to respective medical applications.

3. The drive control device according to claim 1, wherein the parameter specification device selects a control mode, associated to said surgical tool, depending on the employed surgical tool.

4. The drive control device according to claim 1, wherein a predetermined torque/speed characteristic of the electric motor is assigned to each control mode.

5. The drive control device according to claim 1, wherein the parameter specification device determines the respective state of the surgical motor system by preferably continuously detecting the respective instantaneous values of motor current and motor voltage of the electric motor.

6. The drive control device according to claim 5, wherein the parameter specification device determines the temperature of the electric motor by integration of the detected instantaneous values of motor current and motor voltage of the electric motor.

7. The drive control device according to claim 1, wherein at least one control mode provides for a rotational speed regulation of the electric motor and at least one control mode does not perform a rotational speed regulation of the electric motor.

8. The drive control device according to claim 1, further comprising a rotor position determination means for determining a rotor position of the electric motor, wherein, for the determination of the position of the rotor of the electric motor, at least one of the motor windings is cut off from an energy supply for a predetermined time interval.

9. A surgical motor system, comprising:
   an electric motor for driving a surgical tool which can be detachably coupled to said motor directly or indirectly by interposing a tool adapter or a handpiece;
   a drive control device comprising a motor control unit for controlling the electric motor in an open and/or closed loop,
   wherein
   a parameter specification device which is provided upstream of the motor control unit and determines the current medical application on the basis of a detected state or state history of the electric motor of the surgical motor system, selects a control mode which is suitable for said medical application and gives the motor control unit such open or closed loop parameters that the open or closed loop control profile of the electric motor corresponds to the selected control mode.

10. The surgical motor system according to claim 9, further comprising a rotational speed detection means for detecting the actual speed of the electric motor, in particular Hall sensors, and/or a handpiece identification or tool identification means.

11. A method of controlling an electric motor of a surgical motor system in an open and/or closed loop, said electric motor driving a surgical tool,
   said method comprising the steps of:
   detecting a state and/or a state history of the electric motor of the surgical motor system;
   determining the current medical application of the surgical tool on the basis of the detected state or state history;
   selecting a control mode on the basis of the determined medical application; and adjusting the open or closed loop parameters such that the open or closed loop control profile of the electric motor corresponds to the selected control mode.

\* \* \* \* \*